(12) United States Patent
Blechschmidt et al.

(10) Patent No.: US 9,999,696 B2
(45) Date of Patent: Jun. 19, 2018

(54) COMPACT SYSTEM WITH HIGH HOMOGENEITY OF THE RADIATION FIELD

(71) Applicant: Schott AG, Mainz (DE)

(72) Inventors: Jörg Blechschmidt, Zornheim (DE); Michael Kluge, Offenbach (DE); Volker Plapper, Alzey (DE)

(73) Assignee: Schott AG, Mainz (DE)

( * ) Notice: Subject to any disclaimer, the term of this patent is extended or adjusted under 35 U.S.C. 154(b) by 174 days.

(21) Appl. No.: 14/713,195

(22) Filed: May 15, 2015

(65) Prior Publication Data
US 2015/0246148 A1    Sep. 3, 2015

Related U.S. Application Data

(63) Continuation of application No. PCT/EP2013/003432, filed on Nov. 14, 2013.

(30) Foreign Application Priority Data

Nov. 15, 2012   (DE) .................. 10 2012 022 326

(51) Int. Cl.
*A61L 9/20* (2006.01)
*A61L 2/10* (2006.01)
(Continued)

(52) U.S. Cl.
CPC ...... *A61L 2/10* (2013.01); *A61L 9/20* (2013.01); *B01D 53/007* (2013.01); *C02F 1/325* (2013.01);
(Continued)

(58) Field of Classification Search
CPC .................................. A61L 2/10; A61L 9/20
See application file for complete search history.

(56) References Cited

U.S. PATENT DOCUMENTS

| 4,948,980 A | 8/1990 | Wedekamp |
| 5,216,251 A | 6/1993 | Matschke |

(Continued)

FOREIGN PATENT DOCUMENTS

| DE | 38 24 647 A1 | 2/1990 |
| DE | 10 2004 021 585 A1 | 12/2005 |

(Continued)

OTHER PUBLICATIONS

Chinese Office Action dated Dec. 7, 2016 for Chinese Application No. 201380059971.7 (12 pages).
(Continued)

*Primary Examiner* — Sean E Conley
(74) *Attorney, Agent, or Firm* — Taylor IP, P.C.

(57) ABSTRACT

The invention relates to a system for treating gases and/or liquids with radiation or for detecting radiation in gases and/or liquids, including at least one optical system and a reactor. The reactor has a hollow body shape which includes lateral surfaces, connecting parts, and an inner chamber which may be open to the front and rear sides, through which a medium flows or in which the medium is present. The reactor is designed, at least partially, in the form of a radiation reflector and is divided into first and second functional areas. This enables a particularly homogeneous radiation distribution in the inner chamber of the reactor, which increases the efficiency of the treatment or detection. Also, due to this arrangement, the system is more compact.

20 Claims, 8 Drawing Sheets

(51) Int. Cl.
  *C02F 1/32*   (2006.01)
  *B01D 53/00*  (2006.01)
  *G01J 3/02*   (2006.01)
  *F24D 19/00*      (2006.01)
  *C02F 103/02*     (2006.01)
  *C02F 103/04*     (2006.01)
  *C02F 103/32*     (2006.01)

(52) U.S. Cl.
  CPC ...... *G01J 3/0202* (2013.01); *B01D 2259/804* (2013.01); *C02F 2103/026* (2013.01); *C02F 2103/04* (2013.01); *C02F 2103/32* (2013.01); *C02F 2201/3222* (2013.01); *C02F 2201/3227* (2013.01); *C02F 2201/3228* (2013.01); *C02F 2303/04* (2013.01); *F24D 19/0092* (2013.01)

(56) References Cited

U.S. PATENT DOCUMENTS

| | | | |
|---|---|---|---|
| 5,247,178 | A | 9/1993 | Ury et al. |
| 6,337,483 | B1 | 1/2002 | Matschke |
| 6,555,011 | B1 | 4/2003 | Tribelsky et al. |
| 6,614,028 | B1 * | 9/2003 | Cekic ................ A61L 2/0011 250/432 R |
| 6,626,561 | B2 | 9/2003 | Carter et al. |
| 7,511,281 | B2 | 3/2009 | Cooper |
| 2004/0166018 | A1 * | 8/2004 | Clark ................ A61L 9/205 422/4 |
| 2005/0115498 | A1 | 6/2005 | Ingram et al. |
| 2007/0272877 | A1 | 11/2007 | Tribelsky et al. |
| 2010/0143205 | A1 | 6/2010 | Engelhard |
| 2010/0264329 | A1 | 10/2010 | Vardiel et al. |
| 2012/0248332 | A1 * | 10/2012 | Kreitenberg ........ A61L 2/10 250/455.11 |
| 2013/0153514 | A1 | 6/2013 | Stern et al. |

FOREIGN PATENT DOCUMENTS

| | | |
|---|---|---|
| DE | 10 2011 112 994 A1 | 3/2013 |
| GB | 2 334 873 A | 9/1999 |

OTHER PUBLICATIONS

English translation of Chinese Office Action dated Dec. 7, 2016 for Chinese Application No. 201380059971.7 (13 pages).

Notification of Transmittal of Translation of the International Preliminary Report on Patentability dated May 28, 2015 for International Application No. PCT/EP2013/003432 (30 pages).

* cited by examiner

STATE OF THE ART

STATE OF THE ART

COMPACT SYSTEM WITH HIGH HOMOGENEITY OF THE RADIATION FIELD

CROSS REFERENCE TO RELATED APPLICATIONS

This is a continuation of PCT application No. PCT/EP2013/003432, entitled "COMPACT SYSTEM WITH HIGH HOMOGENEITY OF THE RADIATION FIELD", filed Nov. 14, 2013, which is incorporated herein by reference.

BACKGROUND OF THE INVENTION

1. Field of the Invention

The invention relates to a compact system with high homogeneity of the radiation field, compared with arrangements that are known in the state of the art.

2. Description of the Related Art

It is known to use radiation, in particular UV- or IR-radiation for the treatment of water, gasses, in particular air, or surfaces. Particularly known is disinfection with UV-radiation. Relatively wide spread is drinking water treatment with UV-radiation, whereby the bacterial count in the water, subject to the dosage can be reliably and significantly reduced. Microorganisms, such as pathogens, in particular bacteria or viruses, are inactivated through UV-radiation.

The level of efficiency of a treatment system is determined to a large extent by the homogeneity of the created radiation field in which the medium that is to be treated, for example water, is located. In particular in systems with few light sources, achievement of sufficient homogeneity is difficult and usually associated with high efficiency losses. For treatment efficiency it is therefore preferred to provide an as homogeneous distribution of the radiation intensity as possible. A local increase of the radiation intensity is thereby not harmful. However, a locally strongly reduced intensity may result in insufficient treatment. In the case of disinfection by means of UV-radiation, for example germs that flow through these regions during passage through a UV-reactor are not sufficiently deactivated.

Moreover, a compact design of the treatment system is important for applications in areas where there is a significant lack of space, without however entering into compromises in regard to system efficiency. In addition, due to spatial issues and often also due to aspects of cost the number of radiation sources must be reduced as far as possible.

Two conceptual approaches for UV-disinfection are known from the current state of the art:

In the first concept, high compactness of the arrangement is achieved, whereby however at the same time the radiation homogeneity suffers. A typical example of such an arrangement is the coaxial geometry. FIG. 1a illustrates an exemplary embodiment of such a system, as is known from the current state of the art. FIG. 1a shows a top view of a tubular shaped UV-light source 1 that extends perpendicular to the drawing plane, is arranged inside a tube 7 and is surrounded by a medium such as water. UV-light source 1 is thereby protected from the water by a UV-transparent encasement tube 5. Due to the quadratic decrease of the radiation intensity of the UV-light source with the distance, and the additional weakening due to absorption in the medium, an inhomogeneous radiation field results in FIG. 1a.

To clarify the inhomogeneous radiation field from FIG. 1a, the type of the radiation field which results for an arrangement according to FIG. 1a is illustrated in detail in FIG. 1b on the basis of the so-called ray tracing method. In the ray tracing method ray paths originating from the radiation source are calculated, whereby the optical parameter of the penetrated materials, in particular absorption and reflection coefficients are considered. By calculating a high number of statistically produced output rays, the resulting radiation field is mapped. This method is known to the expert from the current state of the art and therefore requires no further explanation.

In FIG. 1b it is shown how the radiation field in the arrangement of FIG. 1a portrays itself, whereby the individual UV light source 1 is arranged in the center, inside tube 7. The two diagrams on the bottom and the right edge in FIG. 1b are sectionals respectively showing the progression of the radiation density. The bottom diagram shows the radiation intensity in a horizontal section through the center of the drawing (z millimeter) and the right diagram shows the radiation intensity in a vertical section through the center of the drawing (y millimeter). Regions through which no medium is conducted are masked out in the drawing. The diagrams therefore illustrate the radiation intensity along the selected sectional planes. A perfectly homogeneous radiation field would result in a flat horizontal line (so-called "hat profile"). A strongly inhomogeneous radiation field results in a strong deviation of the values along the selected section. It can therefore be seen in FIG. 1b that the radiation intensity is at a maximum near the UV-light source and drops off markedly toward the outer edge of the tube. For the arrangement in FIG. 1a a standard deviation of 43% from the mean value of the radiation intensity was calculated according to FIG. 1b. Such a high value proves poor radiation homogeneity of the system. The arrangement according to FIG. 1a therefore is very compact, has however a very inhomogeneous radiation field. A strongly inhomogeneous radiation field means in this case however, that there are regions in which existing germs which flow through these regions during passage through tube 7 are not sufficiently radiated to be rendered inactive, due to the low radiation intensity. The disinfection efficiency is therefore insufficient.

The following are additional exemplary devices for disinfection from the current state of the art which are also designed relatively compact but command insufficient radiation homogeneity:

US 2007/0272877 A1 relates to a radiation device, in particular a UV disinfection device, including at least one reactor for treatment of fluids by way of light radiation, whereby the reactor includes a tube or respectively a channel or a container consisting of a transparent material and surrounded by air. The radiation device includes a fluid inlet, a fluid outlet, and at least one opening or a window which is adapted for the transmission of light into the tube or respectively the channel. Outside the tube or channel a light source is located, having a light generator and a reflector in order to reflect the light that is produced by the light generator in the direction of the window in a predefined angle region. In particular, a cylindrical reactor is provided for this, which can be designed at least partially so that light, in particular UV light impinging on the walls is reflected back into the medium.

U.S. Pat. No. 6,337,483 B1 relates to a germicidal UV chamber for use with air, whereby the UV chamber itself can be in the embodiment of a reflector and preferably has the shape of a ellipsoid cut off at both ends.

The disclosure in U.S. Pat. No. 6,555,011 B1 relates to a method for disinfection and cleaning of liquids and gasses wherein a special reactor design is applied, wherein the reflective side walls contribute to the concentration of the UV radiation during disinfection of liquids and gasses US 2010/0264329 A1 moreover relates to a disinfection device for liquids with the assistance of light, whereby the device includes: a substantially light-transparent tube to disinfect liquid flowing through it; a substantially light-transparent encasement having outside dimensions which are smaller than the inside dimensions of the tube, whereby the encasement in the tube is arranged substantially perpendicular to the axis of symmetry of the tube; as well as a light source which is arranged inside the encasement. A quartz glass tube preferably serves as the reactor and is located inside reflective walls of a reflector.

U.S. Pat. No. 5,216,251 A describes a disinfection and drying device for hands and forearms, whereby UV light is used in a working chamber in order to disinfect pre-heated air from a second chamber that is connected with the working chamber, to then thereby disinfect and dry the hands or arms in a closed chamber. The disinfected medium is utilized in the form of air to disinfect and dry the hands, whereby disinfection therefore occurs in a more or less enclosed space.

In the second conceptual approach according to the current state of the art UV disinfection systems are provided, that indeed produce a relatively homogeneous radiation field, but require an extraordinarily large space for this and are therefore not designed sufficiently compact:

GB 2 334 873 A for example, describes a sterilization device including a multitude of elliptical reflectors. In FIG. 1 of GB 2 334 873 A an elliptical double reflector 1 is arranged around a test tube 2, whereby the test tube is arranged at the common focal point of the reflector. Two mercury lamps 3 are positioned at the other two focal points of the elliptical double reflector 1.

U.S. Pat. No. 5,247,178 A moreover discloses a device for treatment of a fluid by means of radiation of a thin film of the fluid with concentrated light of high intensity. An annular fluid passageway 102 is provided for radiation so that a thin film of the fluid to be radiated is available. On the interior the annular passageway 102 is defined by a shaft 103 whose surface is reflective. Externally the annular passageway 102 is surrounded by a transparent tube 104. An elliptical reflective cylinder 101 is provided, whereby the radiation source is arranged at or near the first focal point of the elliptical cylinder and the medium that is to be radiated is arranged at or near the second focal point, as seen in detail in FIG. 1 of U.S. Pat. No. 5,247,178 A.

According to the teachings of GB 2 334 873 A, as well as of U.S. Pat. No. 5,247,178 A the UV light sources are therefore arranged outside the UV reactor. Through the arrangement of externally positioned reflectors the UV radiation is coupled as uniformly as possible through the UV-transparent reactor wall into the medium. Currently known systems use reflectors for this purpose whose reflective surfaces are generally separated from the UV-transparent reactor wall. The UV-light is distributed outside the medium-conducting UV reactor such that an as homogeneous as possible radiation field inside the UV-reactor results.

From the current state of the art according to DE 38 24 647 A1 a device for radiating media by means of UV light is also known, consisting of a tubular body through which media flows and which consists of an UV-permeable material, and at least two UV light sources with reflectors, arranged axially parallel on the outside, whereby the light sources are flat UV emitters having an elongated, flat-oval cross section with wide and narrow side, whereby the primary axis of the UV light sources are always directed upon the center point of the tubular body's cross section. The UV light sources are arranged annularly and axially parallel around the tubular body through which media flows. According to one design variation the flat emitters fit closely against the tubular body with the narrow side that is facing toward the tubular body. In this configuration, the UV reactor is not in the embodiment of a reflector. The reflectors are exclusively assigned to the UV light sources and do not form any part of the UV reactor itself through which the medium that is to be disinfected flows. The arrangement according to DE 38 24 647 A1 moreover requires a large space due to the UV light sources being positioned on the outside.

Arrangements of this type facilitate a relatively homogeneous radiation field inside the medium that is to be disinfected. However, the large space that is required for radiation distribution is detrimental with these arrangements. Systems according to the second conceptual approach are therefore not suitable for applications with space restrictions.

Systems known from the current state of the art are therefore either compact, but offer insufficient radiation homogeneity; or systems known from the current state of the art achieve indeed high radiation homogeneity, but require a large space for this which rules out applications in confined installation locations.

What is needed in the art is a system wherein the disadvantages of the current state of the art are avoided, in other words a system which provides sufficiently high radiation homogeneity and at the same time has a very compact design.

SUMMARY OF THE INVENTION

The present invention provides a system for treatment of gasses and/or liquids with radiation or for detecting radiation in gasses and/or liquids, including at least one optical system and a reactor. The reactor is designed in the form of a cylindrical hollow body that includes lateral surfaces, a first part or end part connecting the lateral surfaces, possibly an additional part or inlet part connecting the lateral surfaces, as well as an interior chamber which is open toward the front and rear ends and through which the medium flows or in which the medium is present. The reactor may be a flow-through reactor designed at least partially in the embodiment of a reflector (subsequently also referred to as "first reflector") which reflects radiation emitted by or for the optical system into the interior chamber of the reactor. The reactor is divided into two functional regions: a first functional region F1 which is located most closely to the at least one optical system, and a second functional region F2 which is arranged further removed from the at least one optical system than the first function region F1. In the operational state of the system, radiation in the first functional region can spread substantially unimpeded and in the second functional region in essence overlays of the radiation occur. According to a first variation of the invention, in the first functional region F1 of the reactor, the distance between the lateral surfaces of the reactor located opposite one another increases, possibly continuously, with increasing distance to the at least one optical system, providing no recesses and/or indentations in the reactor.

According to a second variation of the invention, the reactor may be divided into two functional regions: a first functional region F1 which is located most closely to the at least one optical system, and a second functional region F2 which is arranged further removed from the at least one optical system, whereby radiation can spread substantially unimpeded in the first functional region and whereby in the second functional region in essence overlays of the radiation occur. The reactor has at least two second functional regions, whereby in the second functional region F2 the distance between the lateral surfaces of the reactor located opposite one another decreases, possibly continuously, with increasing distance to the at least one optical system.

According to another embodiment of the invention, the reactor through which the medium is conducted assumes at the same time the function of a reflector. The homogenization of the radiation field thereby occurs through reflection from the walls of the reactor, and not, as is typical in the current state of the art, outside of same. Due to the fact that the reactor itself functions at least partially as a reflector, the homogeneity of the radiation which is emitted by the optical system or emitted to it, was unexpectedly improved so that a clearly more efficient system is provided.

According to another embodiment of the invention, the optical system may be a light source, especially a UV light source or an IR light source, or an optical measuring device, in particular an optical sensor. A combination of different light sources and optical measuring devices, in particular optical sensors is possible but not absolutely necessary for the improved functionality of the system.

Depending on the optical system that is selected, a system having different functionality is obtained. For example, if the optical system features one (or more) UV light sources, then the system according to that embodiment of the invention is arranged as a UV disinfection system. If the optical system features one (or more) IR light sources, then the system according to that embodiment of the invention is arranged as a heating system. If the optical system features one (or more) optical measuring devices, then the system according to the embodiment of the invention is arranged as a system that is used for example in spectroscopy.

The following explanations apply regardless of which optical system has been selected, provided nothing else is specified. It must be noted that, if the optical system consists of an optical measuring device, in particular an optical sensor, the radiation is emitted from the interior chamber of the reactor from where it spreads and eventually impinges on the optical measuring device. The paths of the individual light rays and thereby the functionality of the invention are, however, independent of the direction of propagation of the rays. For the sake of clarity, the functional principle is described below, predominantly with reference to an optical system consisting of one light source.

Within the scope of the current invention "reactor" is understood to be a chamber not necessarily defined on all sides and which is designed so that under defined conditions treatment of a medium that is to be treated, such as UV disinfection of a medium, for example of water, or the targeted heating of a medium by means of IR radiation, or the capture of radiation through a medium, such as in through-flow spectroscopy takes place. Furthermore, recesses and/or indentations in the reactor, as in DE 10 2011 112 994 A1, in which the optical system is disposed in order to radiate the medium flowing in the interior chamber is avoided.

The number and arrangement of the optical systems are not particularly limited. Possibly only one optical system is provided. However, two or more optical systems may also be provided. Exemplary embodiments include 1 to 8 optical systems, preferably 1 to 6 optical systems, in particular 1 to 5 optical systems, especially preferably 1 to 4 or 1 to 3 optical systems. In the case that UV- or IR-LEDs are utilized as optical systems, clearly more optical systems may be provided according to the invention, for example 100 or more UV- or IR-LEDs. Several optical systems can advantageously be arranged side by side. In addition to the number, size, shape, and function of the optical systems, the selection of a suitable arrangement of the optical systems depends also on the selected shape and size of the reactor, as well as the selected function which is to be fulfilled by the system.

According to an alternative embodiment, the system can be provided with an optical system or systems outside or inside of the reactor. "Outside of the reactor" means that the optical system or systems are not located in the interior chamber of the reactor through which the medium flows. "Inside the reactor" means that the optical system or systems are located in the interior chamber of the reactor where the medium flows.

According to an embodiment of the invention, the reactor is not a unit that is closed off to the outside. Rather, it describes a cylindrical hollow body which is open on both opposite ends which are described herein as the front end and back end of the reactor. On the front end, the medium flows into the reactor and on the back end, the medium flows out. The reactor may therefore be a flow-through reactor. The cylindrical hollow body has two lateral surfaces located opposite one another and having a defined wall thickness and which are closed off in a first part and respectively in an additional part, and which surround an internal chamber. The reactor is thus a hollow cylinder in the form of a straight or tilted generic cylinder. A cylinder with base area and cover area originates from displacement of a flat surface or curve along a straight line which is not disposed in this plane. When the straight lines are perpendicular to the base area and cover area, this describes a straight cylinder. The reactor in the embodiment of a hollow cylinder is not limited on both ends by a base area and cover area as in the case of a generic cylinder, but is designed open. The material that is to be used or treated flows for example in the front end (the omitted base area of a generic cylinder) into the reactor and flows out the back end (the omitted base area of a generic cylinder) out of the reactor. During passage through the reactor in the embodiment of the cylindrical hollow body, the medium can be treated or respectively disinfected or heated.

According to one embodiment of the invention, the hollow cylinder may be derived from a straight generic cylinder. The hollow space in the hollow cylinder that is open toward the front and the back forms the interior chamber of the reactor. The form and size of the reactor can initially be arbitrarily selected within the scope of the current invention, provided that the structural conditions for the intended use permit this. Limits arise only based on the technical viability and handling characteristics.

A part respectively connecting the lateral surfaces, for example an inlet part and an end part connect directly to the lateral surfaces of the reactor, thus forming the reactor. Based on this chosen geometry of the reactor, such overlays of the ray paths occur, that a weakening of the radiation is compensated for by contributions of rays reflected from the walls. The cumulative radiation intensity therefore remains substantially unchanged across the entire reactor. An especially high radiation homogeneity results therefrom over the entire interior chamber of the reactor, thereby achieving improved treatment, or detection efficiency. Such a system is moreover characterized by high compactness.

According to the first variation the invention, the medium conducting component in the embodiment of the reactor is divided into two functional regions. The reactor is arranged such that it consists of a first functional region F1 which is located most closely to the at least one optical system, and a second functional region F2 which is arranged further removed from the at least one optical system. In the first functional region, the radiation which is emitted by the optical system or emitted to it can spread substantially unimpeded. In the second functional region in essence overlay of the radiation occurs. In the first functional region F1 of the reactor, the distance between the lateral surfaces of the reactor located opposite one another increases, possibly continuously, with increasing distance to the at least one optical system. According to this embodiment of the invention it became evident that in order to achieve especially homogeneous radiation intensity, an enlargement of the interior chamber of the reactor in the direction toward the connecting part is provided.

According to an additional embodiment, the reactor is arranged so that the distance between the lateral surfaces of the reactor that are located opposite one another in the second functional region F2 decreases, possibly continuously with increasing distance to the at least one optical system. According to this embodiment of the invention it became also evident that, in order to achieve especially homogeneous radiation intensity it is advantageous if in the second functional region tapering of the interior chamber in the direction of the connecting part is provided. According to this design variation the at least one optical system can be provided outside or inside the reactor.

According to an additional embodiment, the reactor is arranged so that the distance between the lateral surfaces of the reactor that are located opposite one another in the first functional region F1 increases, possibly continuously, with increasing distance to the at least one optical system and that the distance between the lateral surfaces of the reactor located opposite one another in the second function region F2 decreases, possibly continuously, with increasing distance to the at least one optical system. According to this embodiment the at least one optical system can again be provided outside or inside the reactor.

First functional region (F1) may or may not be located in the interior chamber and thus in the medium-conducting region of the reactor. In the first functional region the radiation, viewed from a radiation source, for example in the form of an optical system can spread unimpeded. In this region, functional region 1, the intensity of the radiation decreases with increasing distance from the radiation source, due to the spatial expansion as well as due to a possible absorption by the flowing medium. After a travel distance that is predefined by the geometry of the reactor the radiation then impinges on the reflecting lateral surfaces and is reflected back at an angle. This angle is defined by the geometry of the reactor in such a way that an overlay of the path of the rays occurs. The weakening of the radiation is thereby compensated for by contributions of rays being reflected from the walls, so that the cumulative radiation intensity remains substantially unchanged over the entire second functional region.

Consequently the second functional region (F2), besides the first functional region, is the remaining region in the reactor where, viewed from a radiation source, the interior chamber of the reactor preferably tapers in the direction of the end part. This may occur for example through tilting of the lateral surfaces toward the inside, in other words in opposite direction, by always an appropriate angle of less than 90° from a horizontal plane through the reactor.

The exact form of the medium conducting component in the embodiment of the reactor depends, therefore, on the strength of the radiation absorption of the medium, the reflective characteristics of the lateral surfaces, the minimum radiation density and possible spatial restrictions. The first function region F1 is selected so that the reactor progressively expands with increasing distance to the at least one optical system. In other words, the distance of the lateral surfaces increases, possibly continuously, with increasing distance to the at least one optical system. "Continuously" in this context means that there is no interruption of the lateral surfaces.

According to the variations explained above, the functional regions can therefore be arranged differently.

According to another embodiment of the invention, the distance between the lateral surfaces in the first functional region increases, possibly continuously, with increasing distance to the at least one optical system, and decreases, possibly continuously, in the second functional region with increasing distance to the at least one optical system. The first functional region can then connect to the second functional region, for example through the provision of a structural transition. This transition may for example be an angular shape, such as a corner or edge as provided in both lateral surfaces, or may also be a round shape.

The parts connecting the lateral surfaces, in particular in the embodiment of an inlet part and end part of the reactor, can be selected relatively arbitrarily in regard to shape and size. They only serve to close off the radiation chamber of the reactor to the outside, in other words to connect the lateral surfaces with each other, resulting preferably in a self-contained surface area of the hollow cylinder. The end part of the reactor may be in the embodiment of a reflector, and thereby contribute in addition also to the homogeneity of the radiation field.

The principle according to the invention, according to which the radiation initially spreads in a first functional region in the reactor and wherein then an overlay of the ray paths occurs in the second functional region can be used for systems with exterior or interior optical systems, such as UV light sources, IR light sources or optical measuring devices, in particular optical sensors, wherein in the case of optical measuring devices, in particular optical sensors the radiation spread according to the invention occurs in opposite direction.

If the optical system or systems are located outside the reactor, a predefined radiation-transparent region in the embodiment of a radiation-transparent window in the reactor is preferably provided. This radiation-transparent window may be provided in the inlet part of the reactor, or form the inlet part of the reactor. Through this radiation-transparent window the radiation travels from either one or a plurality of optical systems in the form of one or a plurality of light sources, for example UV or IR light sources, which are arranged on the outside of the reactor into the interior chamber of the reactor which is divided into a first and a second functional region. Alternatively, the radiation travels from the interior chamber of the reactor through this radiation-transparent window to one or a plurality of optical systems in the form of optical measuring devices, in particular optical sensors. The radiation-transparent widow may therefore connect the two lateral surfaces of the reactor in the inlet part, or as the inlet part.

If the optical system or systems are located in the center of the reactor, then the first functional region F1 is located in this case in the interior region of the medium conducting reactor where the radiation can freely spread. The second functional region F2 starts where the first functional region transitions into one or more connecting tapering regions. According to this embodiment of the invention the tapering of the second functional region F2 in the reactor therefore contributes significantly to the homogenization of the existing radiation.

According to the second variation of the invention, the reactor can have at least two second functional regions, wherein in the second functional region F2 the distance between the lateral surfaces of the reactor located opposite one another decreases, possibly continuously, with increasing distance to the at least one optical system. According to this embodiment of the invention, it also became evident that in order to achieve an especially high homogeneous radiation intensity in the systems of the current invention it is advantageous if several second functional regions are available and if in the second functional region always a tapering of the interior chamber of the reactor in the direction toward to the end part is provided. 2, 3, 4, 5, 6 or more second functional regions may for example be provided in the reactor.

The high radiation homogeneity achieved with the inventive systems in the embodiments of the first variation or the second variation can be quantified with the already described ray tracing method. The standard deviation from the mean value of the radiation density in the reactor is according to the invention at <30%, preferably <25%, more preferably <20%, even more preferably <15%, in particular ? 13%, particularly preferably ? 10%. According to these embodiments of the invention values in the range of 10 to 20% are generally achieved. With round shapes for the reactor somewhat higher values are achieved which, however, due to the high compactness and simple production procedure still provide satisfactory results. In contrast, the arrangements from the current state of the art provide in part values of above 40%, so that the inventive systems are superior to these arrangements in regard to homogeneity.

Moreover, especially compact systems are provided according to these embodiments of the invention. This may for example be expressed through the volume share of the medium that is to be used or treated, relative to the total volume of the system. The share of the medium present in the reactor, or to be treated is generally consistent with the interior volume of the reactor. There are however also design variations where this is not so, for example if a part of the interior chamber is not filled with media or media is not flowing through same. In these embodiments of the invention the volume share of the medium of the overall volume is very large. In other words, there is hardly any additional and therefore superfluous space available in the system besides the volume of the medium in the reactor that is used or is to be treated. As a general rule it can be said that the share of volume of media to be used or to be treated, or the share of the volume of interior space of the overall volume of the system according to these embodiments the invention is preferably at least approximately 60%, more preferably at least approximately 70%, particularly at least approximately 80%, even more preferably approximately 90%. The previously explained arrangements from the current state of the art on the other hand offer a share of volume of the medium to be used or treated of the overall volume of the system which is in the range of 10 to 20%, as can be seen from FIG. 1 of GB 2 334 873 A and FIG. 1 of U.S. Pat. No. 5,247,178 A.

For the embodiment of the reactor that is set up with first and second functional regions, round as well as angular cross sections can be used for the overall design. Possible cross sections are round shapes such as circular, elliptical, egg-shaped, pear-shaped or polygonal shapes with rounded corners and deviations thereof. With angular shapes, polygons such as regular or irregular polygons are possible which can be varied in many aspects. From a production engineering point of view rounded geometries can be advantageous for the reflector and thereby the reactor. Although they produce a less homogeneous radiation field to some extent, they can be manufactured in a simple manner and can achieve homogeneity of the radiation distribution that is completely sufficient for many practical applications. The round shapes offer an especially compact design and therefore have significant advantages.

According to one embodiment a combination of several reactors can be provided in the system of the current invention. For example 2, 3, 4, 5 or 6 reactors can be combined. Together, they can complete one aggregate reactor or they can represent individual reactors which are structurally connected. The combined reactors together possibly form one common interior chamber. The reactors that are combined with each other can also provide separate interior chambers in which treatment of the medium for example occurs separately.

According to another embodiment of the invention, the wall thickness of the reactor can initially be adjusted discretionarily. Restrictions exist only in regard to the intended application purpose, the desired shape and size, as well as the desired mechanical strength requirement.

For UV disinfection, that the medium that is to be disinfected, in particular water, is frequently under pressure. For example, in the household sector exterior connection pressures are 4 to 8 bar which can, however clearly drop off subsequently to <1 bar, for example during running a water faucet. In commercial water treatment, the pressures are often substantially higher, so that the reactor, depending on the application purpose and application location, should be designed for specified pressures. A suitable wall thickness for a reactor for the specific application field can readily be selected.

The precise geometry of the reactor, in particular dimensions, angles and the like can therefore be determined and selected depending upon the number, arrangement, and form of the optical systems, the radiation absorption coefficient and the type of medium that is being used, the reflection losses on the reflective surface of the reflector, as well as other loss mechanisms. These factors are therefore to be adapted to the specific application. The shape and size of the reactor is therefore determined, at least in part by the shape and size of the reflector, depending on the design variation. The design of the reactor, at least in part as a reflector, can be provided in a number of different ways:

In one embodiment the entire surface area of the reactor itself, which is the two lateral surfaces, the inlet part, and the end part of the reactor, or parts thereof, can be designed as the reflector. Possibly only one surface or partial surface of the reactor is not designed as the reflector. According to this embodiment of the invention it is preferred if the reactor except for the inlet part is designed as the reflector.

According to another embodiment of the invention, a predefined radiation-transparent region or a radiation-transparent window may be provided in the reactor so that radiation from one or more optical systems, for example in the embodiment of one or more light sources, for example UV or IR light sources, can pass through. The shape and size of the radiation-transparent region or window can be selected and adapted depending on number, size, and shape of the utilized optical systems, so that an appropriately sized "opening angle" is available for the optical system or systems. It is also possible that several radiation-transparent regions or windows are provided in the reactor. Possibly, there is only 1 radiation-transparent window. Possibly one radiation-transparent region is provided respectively in the reactor for each optical system or for a group of optical systems.

A radiation-transparent window may also be provided in the inlet part of the reactor, or form the inlet part, so that the interior chamber of the reactor is separated from the at least one optical system and from a possibly present reflector. The radiation-transparent window is intended to allow radiation to pass from one or more optical systems which are arranged outside the reactor into the interior chamber of the reactor, or radiation from the interior chamber of the reactor to one or more optical systems. If optical systems are provided only inside the reactor, then the entire reactor, that is the lateral surfaces, the end part and possibly present inlet part, can be designed as a continuous reflector. In this case a radiation-transparent region can be provided which surrounds the optical system or systems and which is for example in the embodiment of a radiation-transparent tube in order to protect the optical system or systems from the medium that is being used. For each interior optical system, such a radiation-transparent region is provided in the embodiment of an encasement or a tube.

The material of which the reflector consists is not particularly restricted. Any material or any combination of materials can be used, which is known in the art as being used for a reflector. The reflector can be constructed for example of a flexible or rigid, or solid material. Depending on the specific design, the wall of the reactor can consist partially or completely of a material or a material combination which reflects the light of the selected light source. One example of a material is aluminum.

According to an additional embodiment, the reflector can be applied onto the wall of the reactor in the form of a radiation-reflecting, for example UV- or IR-reflecting, exterior or interior layer or coating. A radiation-reflecting layer or coating can for example be applied to the inside of the reactor wall. In this case the reflector is applied directly onto the inside wall of the reactor or coated on the inside. The material of which the reactor consists is not restricted provided that it is suitable for the application purpose. The radiation reflecting layer or coating can be selected from a multitude of materials or material combinations. For example, a multilayer system may also be utilized. The reflector may for example be manufactured from a cost-effective metal or a cost-effective metal-alloy. Other materials are also possible. The advantage of a radiation-reflecting inner layer or internal coating is that the reflected light is not weakened by the passage through the wall to the reflector due to residual absorption as is the case with an exterior layer or coating.

The radiation-reflecting inner layer or coating can in addition be protected from the medium that is to be disinfected, by a protective layer. This is however not necessary in each case. If, for example water is the medium that is used, then a water resistant material that, for example is UV- or IR-transparent can be used as protective layer or coating.

The reflector may also constitute a radiation reflecting layer or coating on the outside of the reactor. In this case, the reflector is applied directly onto the outside wall of the reactor or is coated onto the outside. Through the provision of an exterior layer or coating, the reactor itself is composed of radiation-transparent material, for example UV- or IR-transparent glass. Such a radiation reflecting layer or coating can consist of a material or a material combination. Multilayer systems may also be used.

The term "radiation-transparent" means that the material that is used according to the invention has a high transmission for certain radiation which means that a transmission of at least 75% exists at an appropriate wavelength of the used radiation, for example a wavelength of 254 nm with UV-radiation, or an appropriate wave length range and a layer thickness of the material of 1 nm.

According to an preferred embodiment, provided that UV-radiation is used, the material at a layer thickness of 1 mm displays a transmission in the UV-range which is around 200 nm<5% and at 254 nm>75%. Even more preferred is a transmission at a layer thickness of 1 mm in the UV-range at 200 nm<1% and at 254 nm>80%. Especially preferred UV-transparent material is for example UV-transparent glass, for example quartz glass.

According to another preferred embodiment, provided that IR-radiation is used, the material displays a transmission at a layer thickness of 1 mm in the IR-range which is higher than 780 nm>75%, and below the range <5%. Especially preferred IR-transparent material is for example quartz glass.

The material of the inventive system is selected according to the selected optical system, for example according to the radiation wave length of the used light source or sources in order to let the appropriate radiation pass through or to reflect it, according to the design form, so that it is not damaged or altered by the radiation. As is known, the material selection when using IR-light sources is much less restrictive than when using UV-light sources. The respectively suitable materials are known from the current state of the art.

In addition to the reactor which is at least partially designed as a reflector, one or more individual reflectors may be provided which are arranged behind the existing optical systems. Hereafter, these additional reflectors are also referred to as lamp reflectors or second reflectors. This embodiment is used especially when the optical system or systems are arranged outside the reactor. Preferably one reflector is assigned to each optical system or to each group of optical systems in order to provide an as high as possible radiation energy for the medium that is streaming or flowing or is present in the reactor. In particular, in the case of an undirected optical system, the provision of one or more reflectors is preferred. The reflector behind the optical system fulfills the function of reflecting light which was emitted in the wrong direction, into the reactor.

The individual reflectors assigned to the respective optical systems may be selected in any discretionary shape. A wide variety of reflector geometries are hereby suitable. Optical radiation homogeneity is achieved if the first and second reflectors are coordinated with each other. The reactor assigned to the optical system may have a round shape, such as a concave mirror in the shape of a spherical sector, or an angular shape. Preferably, the reactor assigned to each optical system envelopes said system in such a way that the radiation emitted from the optical system, for example in the form of a light source, is radiated only in the direction of the reactor. The reflectors may therefore be selected in any discretionary shape, whereby they are arranged open on one side, so that the light from the optical system can be radiated in a substantially preferable direction.

According to an additional design variation, the reactor which is in part in the embodiment of a first reflector, and the second reflector that is assigned to an optical system can be designed and arranged such that they are in contact with each other, or overlap each other in such a way that a kind of aggregate reflector with a common radiation chamber is created. It is to be noted herein that this radiation chamber in an actual sense does not represent an enclosed space, but that it is open on both ends, so that the existing medium can flow in and out. Based on this design according to this embodiment of the invention, a particularly high homogeneity of the radiation distribution can be achieved and in addition, a particularly high compactness of the inventive system is obtained. The second reflector may be in contact with the reactor that is at least partially in the embodiment of the first reflector. The second reflector thus additionally discharges heat due to direct contact with the reactor.

Another embodiment of the system of the invention is represented by the so-called "modified inlet cone". In this embodiment, only one optical system may be provided. However, several optical systems may also be present. The optical system is arranged outside the reactor. The lateral surfaces and the end part of the reactor are in the embodiment of a first reflector. The inlet part of the reactor is embodied by a radiation-transparent window which connects the two lateral surfaces with each other. In one design variation the optical system is a light source, such as a UV- or IR-light source and emits its light through this radiation-transparent window into the interior chamber of the reactor. In another design variation the optical system is an optical measuring device, in particular an optical sensor that captures the light of one or several light sources which are located inside the reactor and whose light passes through the radiation-transparent window that, for example is permeable for IR-radiation or UV-radiation. The end part of the reactor may be formed by an angular shape that connects the two lateral surfaces with each other. In another design the reactor tapers in the end part.

The optical system may additionally be surrounded by a lamp reflector or second reflector in such a manner that, for example light emitted into the wrong direction is reflected into the reactor. The first and the second reflector may be designed so that they form an aggregate reflector. This may occur for example in that the first reflector and the second reflector are in contact with each other or are arranged to overlap.

The reactor is arranged such that it consists of a first functional region F1 which is located most closely to the at least one optical system, and a second functional region F2 which is arranged further removed from the at least one optical system, whereby the radiation emitted from or to the optical system region can spread substantially unimpeded in the first function region and whereby in the second functional region in essence overlay of the radiation occurs. According to the first variation of the invention, the first function system is arranged so that the distance between the lateral surfaces of the reactor located opposite one another increases, possibly continuously, with increasing distance to the at least one optical system. The second functional region may be arranged so that the distance between the lateral surfaces of the reactor located opposite one another decreases, possibly continuously, with increasing distance to the at least one optical system. A structural transition may exist, wherein the first functional region transitions directly into the second functional region. This is represented by a corner or respectively an edge, always on both lateral surfaces, whose tip is always directed outward. There may however also be a continuous transition between the first and second functional region.

In the aforementioned modified inlet cone there are two functional regions in the interior chamber of the reactor, so that the entire interior chamber of the reactor is subject to an extraordinarily homogeneous radiation density. There are no local heavily reduced radiation intensities which could lead to insufficient distribution of the radiation efficiency.

Another embodiment of the invention uses a round radiation-transparent glass tube, for example a UV-transparent quartz glass for the reactor which can be produced especially cost effectively. A first reflector is then applied to the inside or the outside of the glass tube wall. Preferably this would be a radiation-reflecting layer or coating which can be composed of one or several materials. According to another embodiment a second reflector is provided which is assigned to the optical system. This second reflector can be arranged so that it is in contact with the first reflector or connects directly to it. An aggregate reflector is therefore created from the two reflectors. Obviously, more than one optical system may also be provided, whereby, if required, also the corresponding number of reflectors can be added which, together with the reactor can form an aggregate reflector.

If the optical system or systems are selected in the form of light sources, then basically any light sources can be used. For example any type of UV- or IR-light source or also light sources in the visible range can be used. In UV-radiation a wavelength of 253.7 nm is normally utilized. This represents the primary emission wavelength of low pressure UV-lamps and a substantive radiation maximum of other UV-lamps. Therefore, medium pressure, high pressure or low pressure UV-lamps, possibly mercury-vapor medium pressure, high pressure or low pressure lamps are therefore used for example as UV-light sources which emit radiation at a wavelength of around 254 nm. Low pressure UV-lamps, in particular low pressure mercury-vapor lamps are preferred. According to an additional embodiment of the invention, UV-light sources in the form of CCL (cold cathode lamp) may be used. These are based on the proven CCFL-technology (cold cathode fluorescent lamp), whereby the fluorescent coating is foregone; these can be purchased currently on the open market. According to the invention UV-LEDs can also be used. If using UV-LEDs a higher wavelength in the range of 270 nm may be selected, whereby on the one hand the disinfection effect is greater; on the other hand typical UV-transparent glasses have a higher transmission at these wavelengths, which increases the efficiency further.

Any light source that sends out IR-radiation can be considered as an IR-light source. Broadband IR-light sources are thermal radiators, for example light bulbs or radiant heaters. Specifically IR-light sources are for example Nernst-needles and IR-LEDs.

For the optical system light sources may also be used whose radiation is emitted preferably inside a defined emission angle, such as UV- or IR-LEDs which may be arranged for example outside the reactor. The emission angle then determines essentially the selection of the size of the region of the reactor which will be designed to be radiation-transparent. For example, a radiation-transparent window of appropriate width and length may be provided. According to one embodiment, the optical systems in the form of light sources can also be secured on a common support plate or printed circuit board, so that the illumination unit can be produced cost effectively, easily assembled, and replaced. A separate assembly of numerous individual optical systems, for example in the form of light sources for the reactor can therefore be omitted.

If relatively intensely radiant light sources, such as common UV- or IR-flashlights are used as optical systems, it is preferred for cost reasons to use an as small number as possible of optical systems or respectively light sources, possibly 1, to a maximum of 3. If relatively weak light sources such as UV- or IR-LEDs are used as the optical systems, then according to the invention a clearly greater number of light sources, for example 100 LEDs or more, may be used. In each case it is advantageous not to fall below pre-defined minimum radiation intensity in order to guarantee sufficient radiation. This however depends on the particular application.

The optical system or the optical systems may be arranged inside or outside the reactor, parallel to the direction of flow of the medium that is to be used. For example, a UV-tubular lamp as the only UV-light source can be used as the optical system which is arranged inside the reactor or outside the reactor, possibly parallel to the direction of flow of the medium that is to be disinfected, such as water.

If in the inventive system a radiation-transparent material is used, the material may be radiation-transparent glass. The usable radiation-transparent glass is not particularly limited within the scope of the invention. Any glass known to the expert that is accordingly transparent for the utilized radiation may be used. UV-transparent glasses that may be used according to the invention are for example quartz glasses, silica glasses, preferably borosilicate glass or sodium-potassium-barium-silica glasses, especially preferably quartz glasses and borosilicate glasses. Especially preferred glasses are described in DE 10 2011 112 994 A1, the disclosure of which is incorporated in its entirety into the current description. IR-transparent glasses that may be used according to the invention are for example borosilicate glassed, preferably quartz glasses.

The medium that is to be used is not particularly limited according to the invention. Any liquid or any gas or also a mixture of several liquids or gasses, or a liquid or gaseous solution, dispersion or similar, also a mixture of two or more components can be used in the inventive system. An example medium is water. According to one embodiment, gas can also be disinfected; it can be advantageous if this is not air. If particularly aggressive gasses or liquids are to be used an appropriate selection can be made from suitable material compositions.

The present invention may be used as a UV-disinfection system, wherein the optical systems includes at least one UV-light source, in particular for disinfection of liquids and/or gasses in a stationary or flowing state, in particular for drinking water treatment and disinfection, disinfection of ultrapure water, waste water, liquids from the pharmaceutical sector and food sector, or for disinfection of gasses such as air or industrial gasses. The present invention may further be used as a heating system, in particular as a continuous flow heater, wherein the optical system comprises at least one IR-light source, in particular for heating of liquids and/or gasses in stationary or flowing state. The present invention may also be used in through-flow spectroscopy, wherein the optical system includes at least one optical measuring device, in particular an optical sensor.

In through-flow spectroscopy light emitting materials are guided through a reactor. The emitted radiation is then detected. A possible field of application is detection of biomarkers or tracers, for example in connection with fluorescein or uranine. The stimulating light source of a specific wavelength generally used additionally for the spectroscopy can easily be integrated into the inventive system. In the case of uranine for example use of a UV-light source and an optical measuring device, in particular optical sensors for green light.

The advantages of the invention are extraordinarily multi-facetted. According to one embodiment of the invention, a system is provided for treatment of gasses and/or liquids with radiation, or for detection of radiation in gasses and/or liquids, wherein the reactor is designed at least in part in the embodiment of a reflector that reflects the radiation provided by one or more systems or for one or more systems into the interior chamber of the reactor. The medium-conducting component in the embodiment of the reactor therefore assumes the function of the reflector at the same time. The compactness of the provided system is thereby improved, since spatially demanding reflector geometries can be omitted. Only additional second reflectors that are assigned to the optical system or systems may be used.

By dividing the interior chamber of the reactor into a first and a second functional region, as described previously, it can be achieved that the weakening in the radiation with increasing distance from an optical system can be compensated for by rays reflected by the walls, so that the cumulative radiation intensity remains substantially unchanged over the entire functional region F1 and F2, thereby again achieving an especially high radiation homogeneity over the entire reactor. Due to the design of the reactor wherein in functional region F1 the distance between the lateral surfaces of the reactor located opposite one another increases, possibly continuously, with increasing distance to the at least one optical system, particularly high radiation homogeneity can be achieved over the entire interior chamber. Also, the additional provision of tapering in the direction toward the end part of the reactor in one or several second functional regions contributes to a large extent to homogeneity of the radiation, for example UV- or IR-radiation.

According to another embodiment of the invention it can be determined with the ray tracing method that the standard deviation from the mean value of the radiation density according to the invention is <30%, preferably <25%, more preferably <20%, even more preferably <15%, and is in particular ≤13%, especially preferably ≤10%. Arrangements from the current state of the art clearly show greater and thereby poorer values in the range of 40% or higher.

Moreover, especially compact systems are provided according to the invention. The share of volume of the medium that is used or treated, for example disinfected or heated, or the share of volume of the interior chamber relative to the overall volume of the system according to the invention is preferably at least approximately 60%, preferably at least approximately 70%, in particular preferably at least 80%, more especially preferred at least approximately 90%. Arrangements with high radiation homogeneity from the current state of the art in comparison offer a share of volume in the region of 10 to 20% of used or treated medium relative to the total medium of the system. The inventive system therefore makes possible a more homogeneous radiation field within the used medium, whereby in contrast to the current state of the art there is no large space requirement for radiation distribution. The inventive system is nevertheless designed relatively simply and avoids unnecessary space. The combination of high homogeneity of the radiation and greater compactness of the system leads to effective results in the current invention, such as a higher disinfectant effectiveness when using UV-radiation or quicker and better homogeneous heating when using IR-radiation or better detection when using optical measuring devices.

The inventive system is moreover extremely selectively variable. The optical systems can be located inside or outside the reactor. The system can be adapted in a targeted manner to a specific application. Due to the fact that the reactor functions at least partially as a reflector and, together with the reflector or reflectors for each optical system can potentially form an aggregate reflector, the provided radiation is put to optimum use.

The functionality of the inventive system can be selected depending on the selected optical system or systems. If UV-light sources are selected as the optical systems, then a UV-disinfection system is obtained that, due to the homogeneity of the produced radiation field has an especially high efficiency level and due to the compact design can be used also in spatially restricted applications. If IR-light sources are selected for the optical systems instead of UV-light sources, the inventive system operates as a heating system, possibly as a continuous flow heater. According to this embodiment, water can for example be heated very efficiently in this manner in a compact space. One advantage of this embodiment according to the invention is in particular the uniform heating in the reactor, in other words over the entire interior chamber, based on the homogeneity of the radiation achieved by the current invention. Subsequent intermixing can therefore be omitted. This may be advantageous in particular if the medium that is to be heated represents a mixture, for example one or several non-organic or organic compounds which are present in a dissolved state or are distributed in a liquid, for example water. In the case of a continuous flow heater the medium flowing through it is radiated with equivalent IR-radiation during its passage, so that uniform and fast heating can be performed.

The materials used are adapted to and selected in consideration of the respectively selected radiation, so that the respective radiation can pass through or be reflected, depending on the design variation and the used material is not damaged or altered by the radiation.

If the selected optical systems are optical measuring devices, in particular optical sensors, the inventive system is suited for example for spectroscopy. The special geometry of the inventive system provides that the same amount of radiation from light-emitting objects, for example fluorescent or phosphorescent materials which are located inside the reactor impinges upon an optical measuring device, regardless of the precise location in the reactor. This provides a measuring signal or respectively sensor signal that is independent from the location of the light-emitting objects, thereby for example making a more precise determination of the number of light-emitting objects possible. This allows for example provision of systems for through-flow spectroscopy.

It is also very advantageous that the inventive system can operate without external influence. The inventive system can be accommodated in a compact housing. The system can be utilized without problems in larger units, for example with flowing medium in a pipe system or also with inactive medium, for example in a tank or similar units. The system can be utilized stationary, permanently installed as part of a larger system or flexibly, or can be a handheld device.

The device according to the invention thereby achieves an as high as possible level of efficiency with relatively low cost expenditure in manufacture. The device according to the invention is also suitable for very specialized applications. For example as a UV-disinfection system in the production of ultrapure water which is used in particular in the pharmaceutical, cosmetic and semiconductor industries, as a heating system for quick and homogeneous heating, or in spectroscopy. The system of the current invention demonstrates its advantages also with smaller systems with high compactness.

BRIEF DESCRIPTION OF THE DRAWINGS

The above-mentioned and other features and advantages of this invention, and the manner of attaining them, will become more apparent and the invention will be better understood by reference to the following description of (an) embodiment(s) of the invention taken in conjunction with the accompanying drawing(s), wherein:

FIG. 1b shows the radiation field of the prior art arrangement illustrated in FIG. 1a;

FIG. 2b shows a section view of the embodiment of the current invention illustrated in FIG. 2a;

FIG. 2c shows a schematic depiction of a ray path of the arrangement illustrated in FIG. 2a;

Figure 1A:
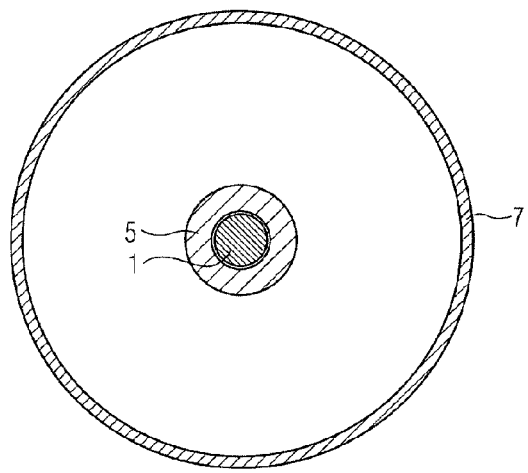
FIG. 1a shows a section view of an embodiment according to the current state of the art, based on coaxial geometry.

The various elements illustrated in the drawings are only representative and are not necessarily drawn to scale. Certain sections thereof may be exaggerated, whereas others may be minimized. Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1B:
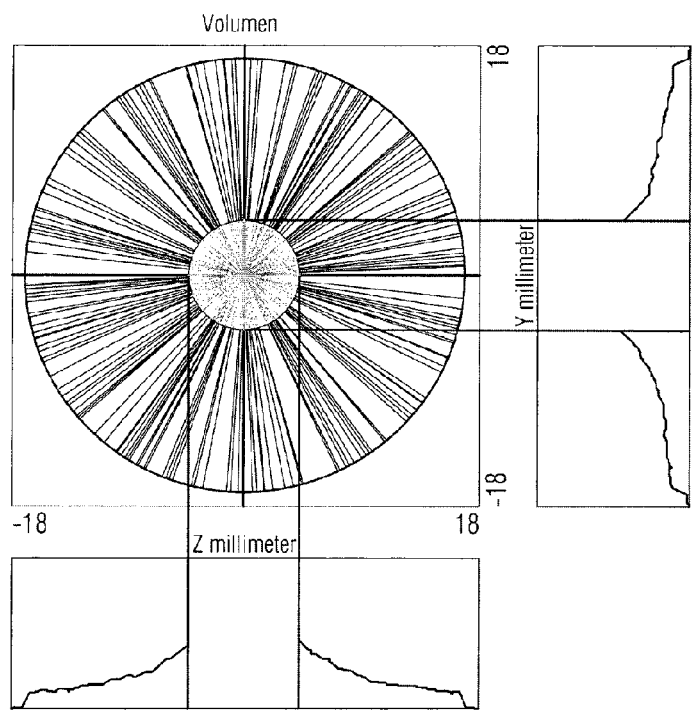

FIGS. 1a and 1b were already discussed in the description of the related art.

Figure 2A:
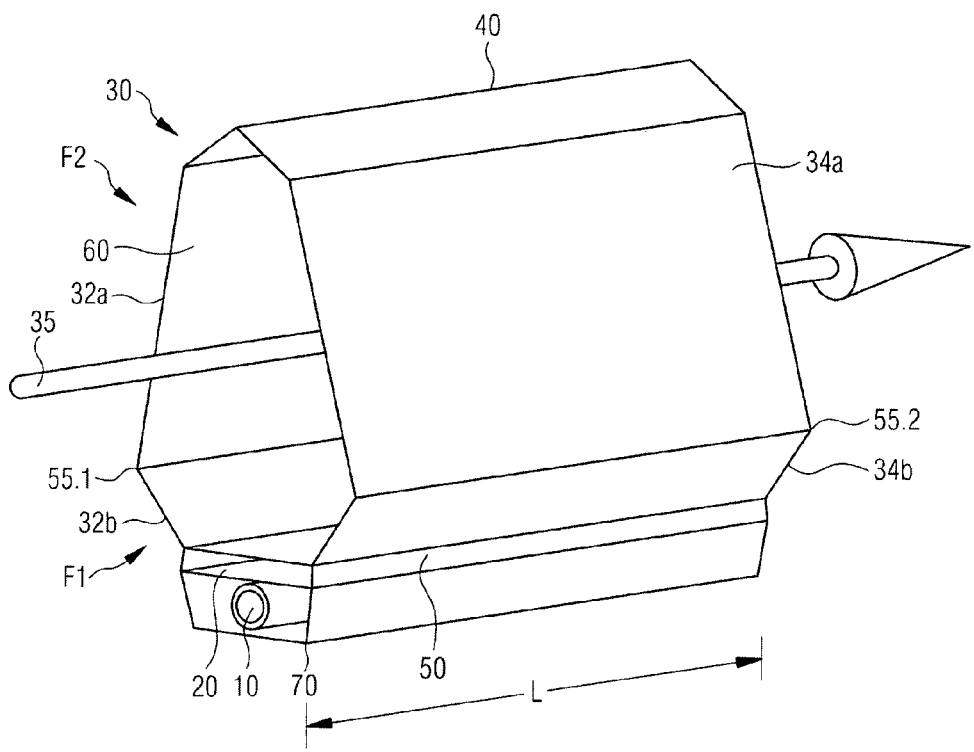
FIG. 2a shows a perspective view of an embodiment of the current invention.

FIG. 2a illustrates a three-dimensional view of an exemplary embodiment of the current invention for visualization of the spatial geometry. The illustrated embodiment of the current invention shows the so-called "modified inlet cone". Illustrated reactor 30 shown in the example is a flow-through reactor. The utilized material flows from the front end to the rear end of reactor 30, through interior chamber 60 which is open on both ends. Arrow 35 symbolizes the direction of flow inside reactor 30. The medium may for example be water. However, other media is also possible. Lateral surfaces 32a, 32b, 34a, 34b as well as connecting part 40 of reactor 30 are always designed as a reflector. This can be implemented either through proper selection of the wall material or through application of a radiation-reflecting layer or coating onto the inside or outside of lateral walls 32a, 32b, 34a, 34b and connecting part 40 of reactor 30. If an outside layer or coating is provided, the wall material is selected from a radiation-transparent material, for example radiation-transparent glass. According to the invention, reactor 30 is thus realized as a reflector, with the exception of one region in inlet part 50 of reactor 30.

In FIG. 2a connecting part 40 is located on top of reactor 30 and inlet part 50 is located at the bottom of reactor 30; this however is not absolutely necessary. Other arrangements are also possible. Inlet part 50 describes the component connecting lateral surfaces 32b and 34b of reactor 30 that is arranged more closely to the at least one optical system 10, in other words is located at a lesser distance from optical system 10 than connecting part 40. Connecting part 40 describes the component connecting lateral surfaces 32a and 34a of reactor 30 that is arranged further away from the at least one optical system 10, in other words is located at a greater distance from optical system 10 than inlet part 50.

The modified inlet cone in FIG. 2a shows the medium conducting component in the embodiment of reactor 30 that is divided into two functional regions F1 and F2. Reactor 30 is hereby designed so that it consists of a first functional region F1 which located most closely to the at least one optical system 10, and a second functional region F2 which is arranged further removed from the at least one optical system, for example in the embodiment of a UV- or IR-light source 10. First functional region F1 is hereby characterized in that the radiation spreads substantially unimpeded and second functional region F2 is characterized in that essentially overlays of the radiation occur.

Figure 2B:
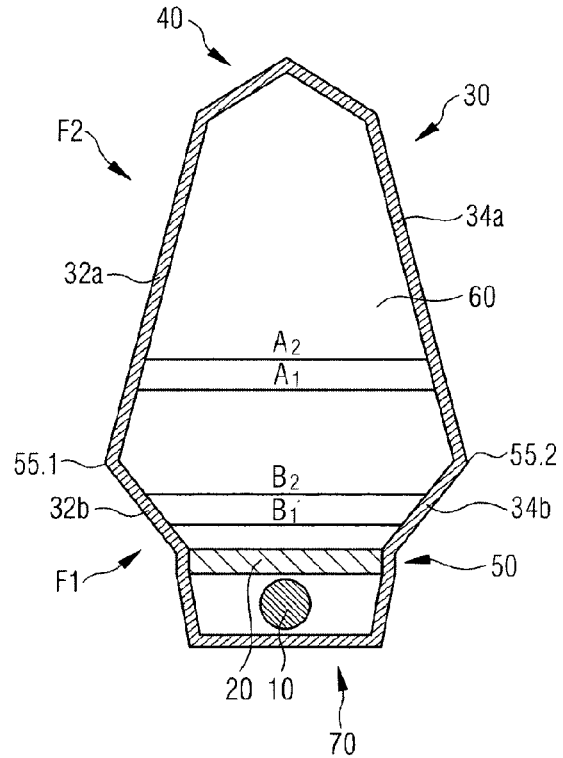

In the illustrated embodiment according to the current invention the first functional region F1 is designed so that the distance between lateral surfaces 32b and 34b of reactor 30 located opposite one another increases, possibly continuously, with increasing distance to the optical system, for example in the form of a light source 10 (distance B2>distance B1, see FIG. 2b). The second functional region F2 is designed so that the distance between lateral surfaces 32a and 34a of reactor 30 located opposite one another decreases, possibly continuously, with increasing distance to the optical system, for example a light source 10 (distance A1>distance A2, see FIG. 2b).

In the illustrated embodiment a structural transition 55 is provided, wherein the first functional region transitions into the second functional region. In this case this always represents a corner or respectively an edge 55.1 and 55.2 that respectively divide the lateral surfaces into 32a and 32b or respectively 34a and 34b.

In the illustrated embodiment, inlet part 50 of reactor 30 forms a radiation-transparent region in the embodiment of a radiation-transparent window 20 that connects the two lateral surfaces 32b and 34b with each other and closes off reactor 30. Through this radiation-transparent window 20, optical system 10 can radiate light into interior chamber 60 of reactor 30, if the optical system is a light source, or receive and detect, if the optical system is an optical measuring device, such as an optical sensor. Other than the illustrated geometries, shapes and dimensional conditions of the window are possible. Optical system 10 is herein located outside reactor 30. Obviously, several optical systems could also be provided which, in the current example would preferably be arranged adjacent beside one another. Optical system 10 in the current example is a UV-light source. The inventive system in this case is therefore a UV-disinfection system. A reflector, lamp reflector or second reflector 70 is assigned to the optical system in the form of UV-light source 10, so that light that is emitted in the wrong direction is reflected into reactor 30.

In the illustrated embodiment reflector 70 could also be omitted. One or several directed UV-light sources 10 could then be advantageously utilized. In the illustrated exemplary embodiment, optical system 10 is shown as a UV-tubular lamp which is arranged parallel to the direction of flow, arrow 35, outside reactor 30. The UV-tubular lamp extends hereby over the entire length L of UV-reactor 30. Other construction methods are possible. The number and arrangement of the UV-light sources is discretionarily variable. Optical system 10 could also be an IR-light source or an optical measuring device, in particular an optical sensor.

UV-transparent region 20 in the current design example is provided between light source 10 and interior chamber 60 of reactor 30 in the embodiment of a UV-transparent window 20. The UV-transparent material can for example be glass. UV-transparent window 20 protects light source 10 from the medium that is to be treated and that flows through interior chamber 60 of reactor 30. The dimensions of the window can be coordinated with the dimensions and the shape of reactor 30 and the utilized optical system 10 can be adapted to them. The UV-transparent region or UV-transparent window 20 in the illustrated example extends over the entire length L of reactor 30. This is however not necessary in all cases. Other geometries are also conceivable.

The dimensions and the shape of the UV-transparent region of window 20 are selected in such a manner that the radiation emitted from light source 10 can enter in the greatest possible extent into interior chamber 60 of reactor 30. Light source 10 in the illustrated example is a UV-tubular lamp in other words an undirected light source. For this case it is preferred to provide a lamp reflector 70. Obviously more than one UV-light source can be used according to the invention. Other lamp types are also possible. For example, instead of the UV-tubular lamp, UV-LEDs could be used. These are directed light sources, so that a lamp reflector could be omitted in this case without jeopardizing the desired homogenous radiation distribution.

In the illustrated embodiment of the current invention the first reflector which consists of lateral surfaces 32a, 32b, 34a, 34b and end part 40 is in direct contact with second reflector 70. In other words, it connects directly to it so that from the two an aggregate reflector is created through which the medium that is to be disinfected flows through interior chamber 60. This results in contact cooling of second reflector 70.

FIG. 2b is a section of the exemplary embodiment of a UV-disinfection system illustrated in FIG. 2a according to the current invention in the shape of an inlet cone as has already been described in detail for FIG. 2a.

Figure 2C:
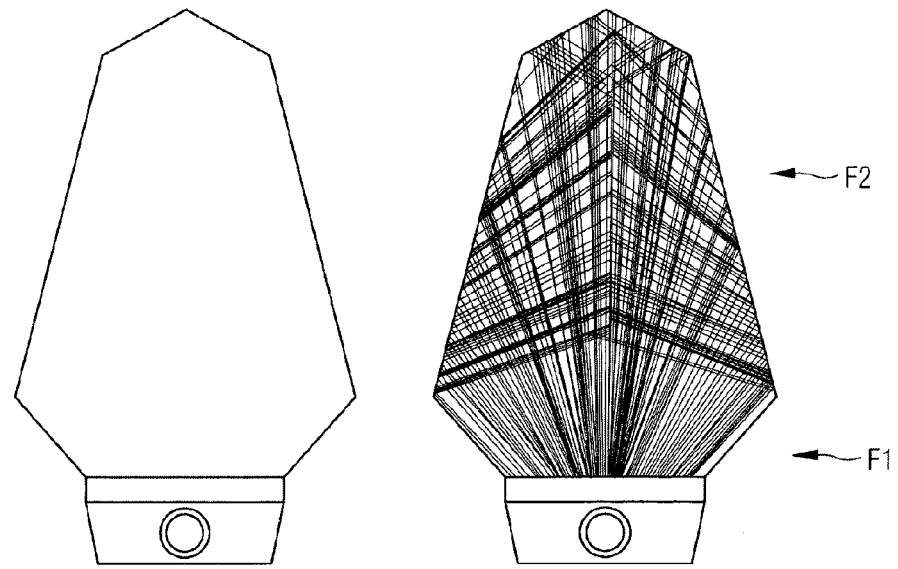

FIG. 2c is a schematic illustration of the ray path of radiation being emitted from an optical system, for example in the embodiment of a UV-light source 10, according to FIG. 2a or 2b. In the region directly behind inlet window 20 the occurring radiation spreads initially. In this region, first functional region F1, the intensity decreases with increasing distance from radiation source 10, due to the spatial spread as well as due to a possible absorption by the existing medium. After a travel path that is defined by the geometry of reactor 30, the radiation impinges then onto reflecting side walls 32a and 34a and is reflected back at an angle. This angle is defined by the geometry of reactor 30 in such a way that in second functional region F2 essentially an overlay of the ray paths occurs. The weakening of the radiation is thereby compensated for by contributions of rays being reflected from the walls, so that the cumulative radiation intensity remains substantially unchanged over the entire second functional region. The illustrated corner or respectively edge, always in the lateral surface represents the transition from the first into the second functional region.

The UV-lamp shown in FIGS. 2a to 2C can be exchanged with an IR-light source. In this case, an inventive heating system would result. If the UV-light source would be replaced by an optical measuring device in particular an optical sensor, then the resulting inventive system could be utilized in spectroscopy, wherein one or several light sources would be located inside the reactor.

On the basis of a simulation with the so-called ray tracing method, ray paths originating from the optical system in the embodiment of a radiation source 10 are calculated for FIGS. 2a and 2b, whereby the optical parameters of the permeated materials, in particular the absorption and reflection coefficients are considered. By calculating a high number of statically created output rays the resulting radiation field is mapped. From FIG. 2c it is therefore seen that the radiation intensity provides high homogeneity of the radiation intensity over the entire interior chamber 60 of reactor 30. In order to quantify this, a standard deviation of 10% from the mean value of the radiation density was calculated for the second functional region for the arrangement of FIGS. 2a and 2b. Such a low value substantiates especially high radiation homogeneity of the system in FIGS. 2a and 2b. The radiation near the light source in the first functional region is very strong, so that the required radiation value is achieved in each case for an appropriate application.

As can also be seen from FIG. 2a the share of the volume of medium that is to be disinfected, in the current case the volume of interior chamber 60 relative to the overall volume of the system is very large and amounts to more than 80%. Consequently, this embodiment of the current invention in the form of a UV-disinfection system, based on the shape of the modified inlet cone according to FIG. 2a or 2b, provides high radiation homogeneity as well as great compactness of the system, resulting in an improved and thereby an extraordinary high overall efficiency of the system.

Figure 3A:
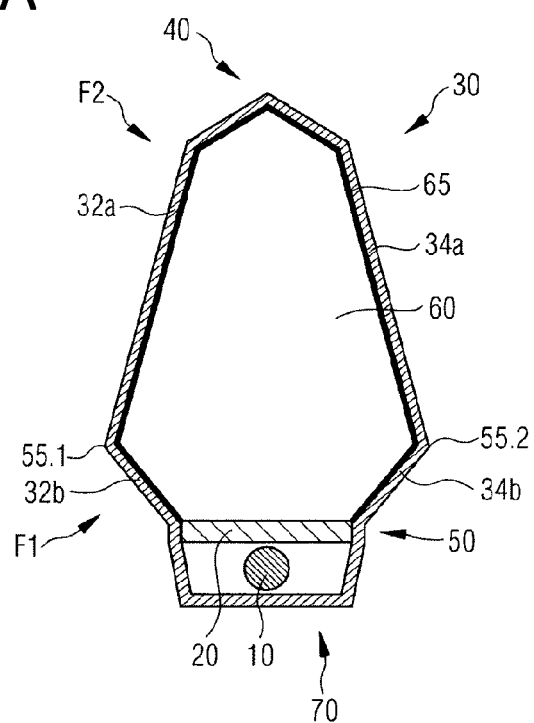
FIGS. 3a and 3b each show a section view of additional exemplary embodiments of the system according to the current invention.
Figure 3B:
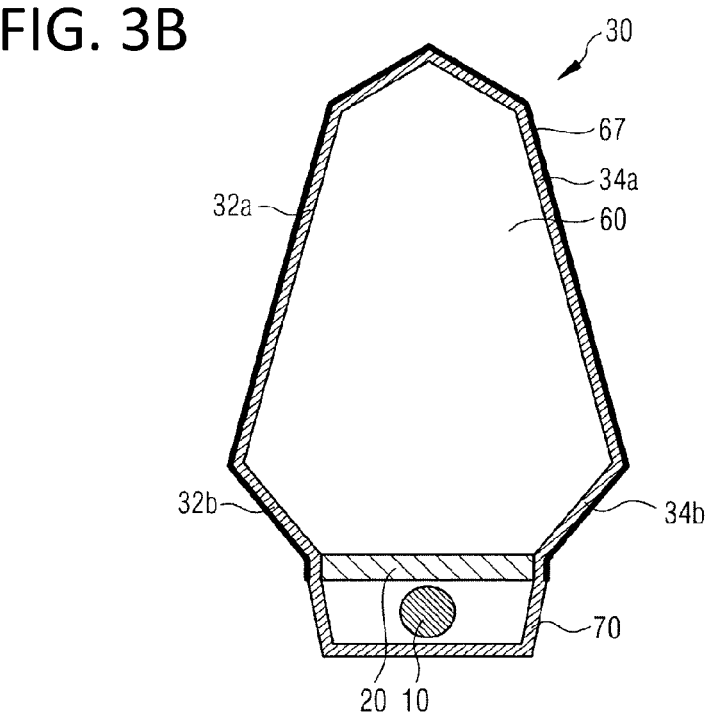

FIGS. 3a and 3b each illustrate a section view of additional exemplary embodiments of the system according to the current invention. The modified inlet cone is illustrated, whereby lateral surfaces 32a, 32b, 34a, 34b and connecting part 40 can be designed as reflector in different variations. In FIG. 3a, a radiation-reflecting interior layer or coating 65, and in FIG. 3b, a radiation-reflecting outside layer or coating 67 is provided. Optical system 10 can be a light source, in particular a UV- or IR-light source, or an optical measuring device, in particular an optical sensor.

Figure 4A:
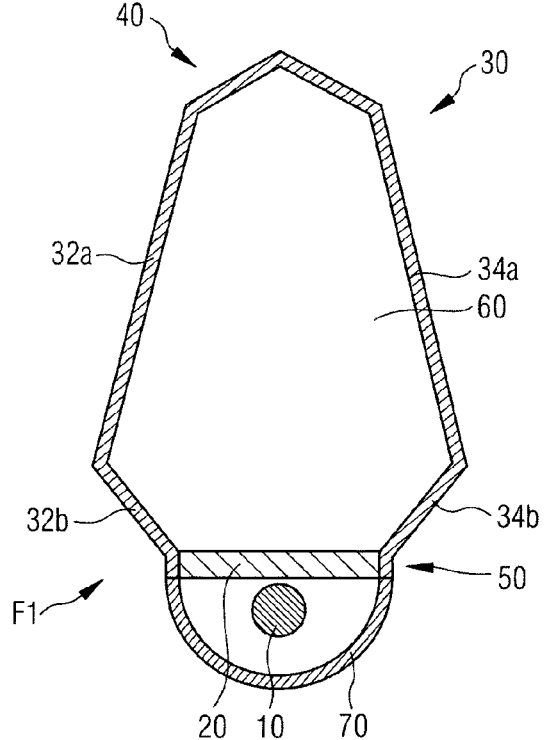
FIGS. 4a and 4b each show a section view of additional exemplary embodiments of the system according to the current invention.
Figure 4B:
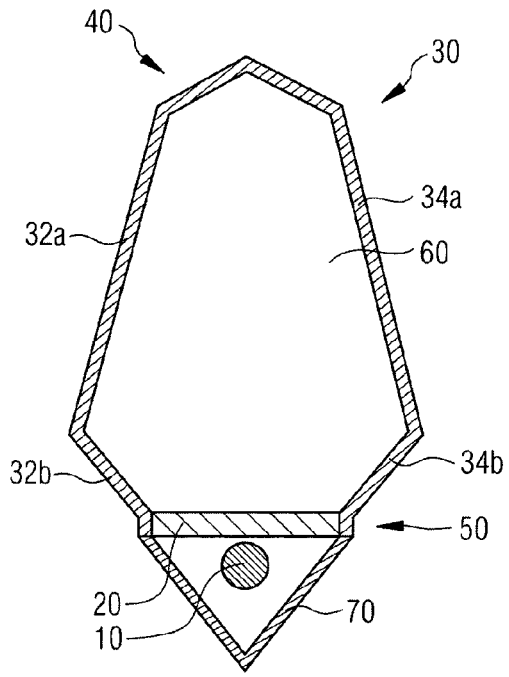

FIGS. 4a and 4b each illustrate a section view of additional exemplary embodiments of the system according to the current invention, whereby the shape of reflector 70 was varied. In FIG. 4a reflector 70 has a round shape. The example is of a concave mirror in the shape of a spherical sector. In FIG. 4b reflector 70 has an angular shape. Other cross sections and geometries with a number of optical systems other than that shown are of course also possible.

Figure 5A:
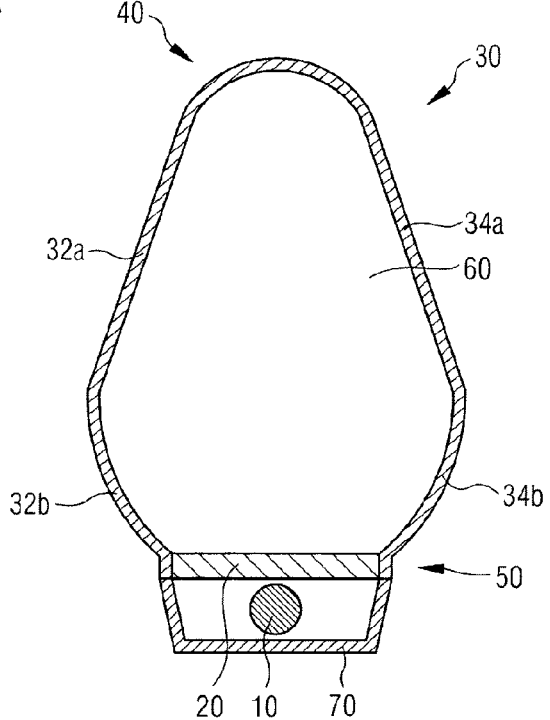
FIGS. 5a and 5b each show a section view of additional exemplary embodiments of the system according to the current invention.
Figure 5B:
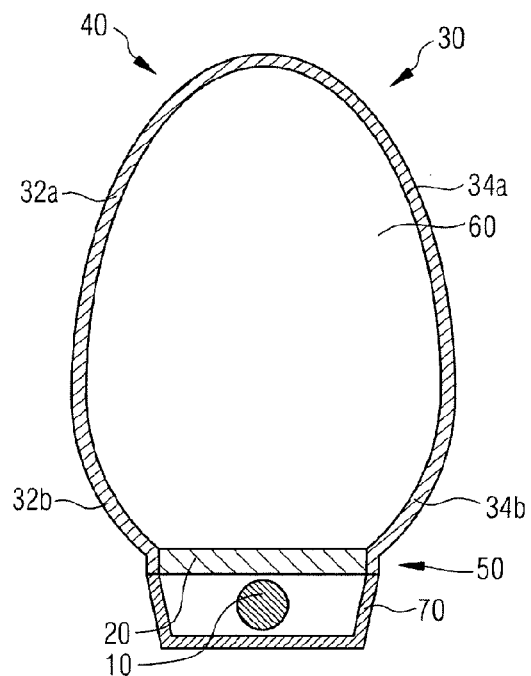

FIGS. 5a and 5b each illustrate a section view of additional exemplary embodiments of the system according to the current invention, whereby the shape of reactor 30 was modified. In FIG. 5a reactor 30 is pear-shaped. In FIG. 5b the reactor is egg-shaped. Other cross sections and geometries with a number of optical systems other than that shown are of course also possible.

Figure 6A:
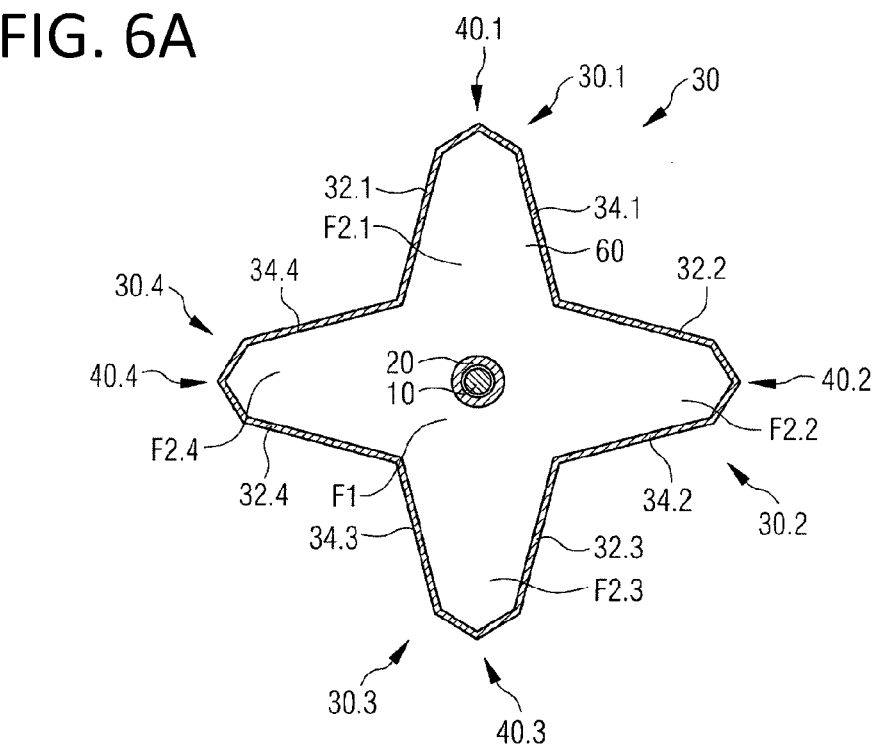
FIGS. 6a and 6b each show section view additional exemplary embodiments of the system according to the current invention.
Figure 6B:
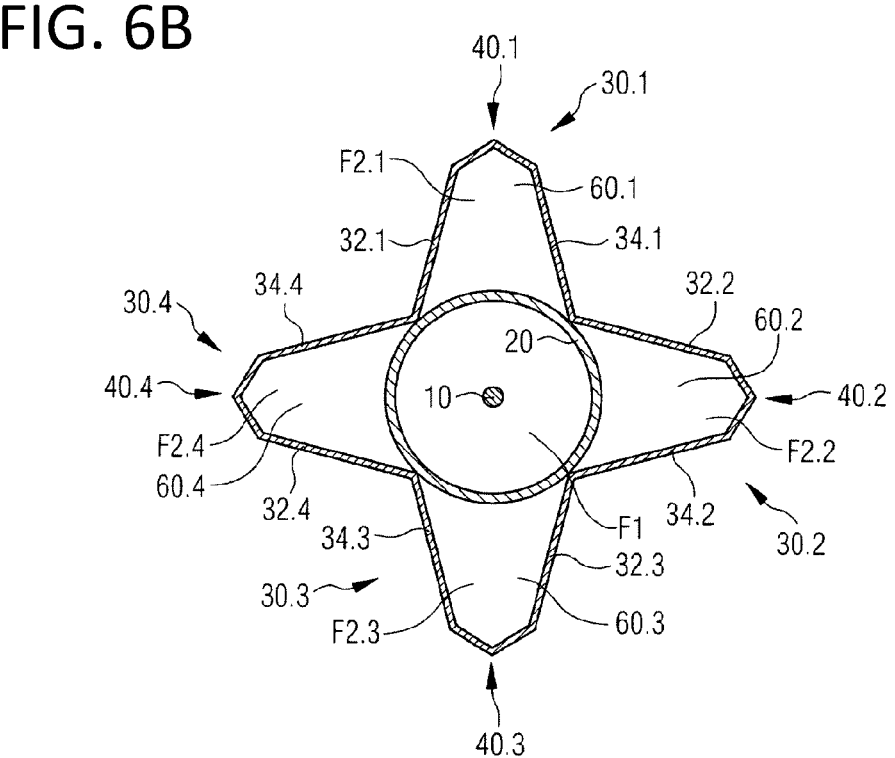

FIGS. 6a and 6b each illustrate a section view of additional exemplary embodiments of the system according to the current invention. FIG. 6a is a section view of an exemplary embodiment of the system according to the current invention, whereby optical system 10, rather than in the previously shown embodiments, is arranged in interior chamber 60 of reactor 30, preferably in its center. The illustrated design variation is therefore very compact. The illustrated shape is derived from the basic shape of the modified inlet cone according to FIG. 2b, whereby several reactors are combined. In the illustrated example 4 reactors 30.1, 30.2, 30.3, 30.4 which are grouped around optical system 10 are combined into one reactor 30. Other combinations with less or more than 4 reactors and other geometries are also conceivable. Optical system 10 that is arranged preferably in the center of interior chamber 60 of reactor 30 is surrounded by a radiation-transparent region 20 which, for example is composed of glass that permits the appropriate radiation to pass through. Lateral sides 32.1, 32.2, 32.3, 32.4 and 34.1, 34.2, 34.3, 34.4 as well as connecting parts 40.1, 40.2, 40.3, 40.4 are designed as reflectors in known and already discussed variations.

In the illustrated embodiment aggregate-reactor 30 is preferably arranged so that 4 reactors 30.1, 30.2, 30.3 and 30.4 are provided whereby each is composed of a first functional region F1, which is located most closely to the at least one optical system, and a second functional region F2 which is located further removed from the at least one optical system. Hereby each of the reactors is arranged so that the distance between lateral surfaces (32.1 and 34.1; 32.2 and 34.2; 32.3 and 34.3; 32.4 and 34.4) of the reactor respectively located opposite one another decreases with increasing distance from the at least one optical system in second functional region F2. Thus, first functional region F1 in FIG. 6a is situated in interior chamber 60 of reactor 30 through which the medium flows perpendicular to the drawing plane, wherein the radiation can spread freely. Second functional region F2 starts where the primary chamber divides into several connecting tapering regions F2.1, F2.2, F2.3 and F2.4.

FIG. 6b is a section view of an additional exemplary embodiment of the system according to the current invention, whereby optical system 10 is arranged in interior chamber 60 of reactor 30, preferably in the center. Rather than is the case in FIG. 6a, in FIG. 6b transparent region 20 is not arranged directly around optical system 10, but instead at a distance thereof which was selected large enough that it encompasses first functional region F1. Individual reactors 30.1, 30.2, 30.3 and 30.4 are thereby separated from each other and are not combined into an aggregate-reactor. The utilized medium does not flow through the first functional region, but instead only in reactors 30.1, 30.2, 30.3 and 30.4. The space between optical system 10 and radiation-transparent region 20 is therefore empty. This can contain a vacuum or a gas, or air having preferably low radiation absorption. Interior chambers 60.1, 60.2, 60.3 and 60.4 of reactors 30.1, 30.2, 30.3 and 30.4 each have a second functional region wherein the overlay of the ray paths occurs. These arrangements are similar to the modified inlet cone according to FIG. 2a whereby radiation-transparent window 20 for each reactor 30.1, 30.2, 30.3 and 30.4 is in the shape of a section of a circular hollow cylinder that in the aggregate complete a circular hollow cylinder. However, the lateral surfaces each exhibit a decreasing distance in direction of respective connecting part 40.1 to 40.4. The illustrated arrangement offers high radiation homogeneity, whereby losses at a reactor behind the optical system are generally eliminated.

Figure 6C:
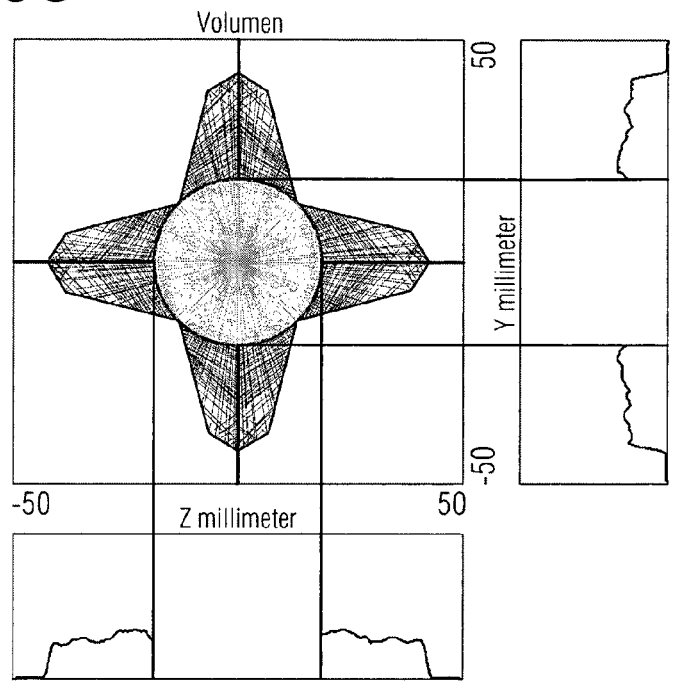
FIG. 6c shows a schematic depiction of the radiation field of the arrangement illustrated in FIG. 6b.

FIG. 6c is a schematic illustration of the radiation field of the arrangement in FIG. 6b by use of a simulation with the so-called ray tracing method. The two diagrams at the bottom and right edge in FIG. 6b respectively show the progression of the radiation intensity along the horizontal section through the center of the drawing (lower diagram, z millimeter) and in a vertical section through the center of the drawing (right diagram, y millimeter). Non-medium conducting regions are masked out in the illustration. The diagrams illustrate the radiation intensity along the selected sectional plane. A perfect homogenous radiation field would result in a flat horizontal line ("hat profile"). A strongly inhomogeneous radiation field results in a strong deviation of the values along the selected section. FIG. 6c demonstrates therefore that the radiation intensity provides high homogeneity of the radiation intensity over all interior chambers 60.1, 60.2, 60.3 and 60.4 of the 4 reactors 30.1, 30.2, 30.3 and 30.4. In order to quantify this, the standard deviation from the mean value of the radiation density was calculated with 13% for the arrangement in FIG. 6a according to FIG. 6b. Such a low value substantiates especially high radiation homogeneity of the system.

As is seen in FIG. 6b the share of volume of the medium that is used or treated in the current case the volume of interior chambers 60.1, 60.2, 60.3 and 60.4, relative to the overall volume of the system is relatively large and is greater than 60%. Accordingly, the 4-times combination based on the shape of the modified inlet cone according to the current invention possesses high radiation homogeneity as well as also high compactness of the system, thus resulting in improved overall efficiency of the system.

Figure 7:
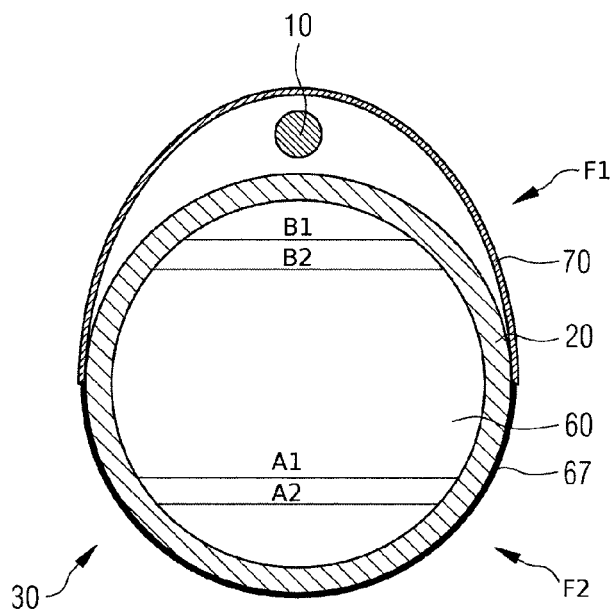
FIG. 7 shows a section view of an additional exemplary embodiment of the system according to the current invention.

FIG. 7 is a section view of an additional exemplary embodiment of the system according to the current invention. Illustrated reactor 30 in the current example is in the embodiment of a radiation-transparent circular tube, for example a radiation-transparent glass tube. The utilized medium flows through the glass tube in a perpendicular direction relative to the drawing plane. The medium may for example be water. However, other media are also conceivable. In the illustrated example a radiation-reflecting layer or coating 67 is applied onto the wall of reactor 30. This coating 67 constitutes the first reflector. In the illustrated example, optical system 10 is shown in the embodiment of an IR-light source that is arranged parallel to the direction of flow, outside reactor 30. The IR-lamp extends preferably along the entire length L of reactor 30. Other construction methods are possible. The number, arrangement as well as the type of optical systems are discretionarily variable. Optical system 10 is surrounded by a second reflector 70, which in this case constitutes the so-called lamp reflector. In the illustrated embodiment, second reflector 70 is in the form of a concave mirror. Other forms are of course also possible.

Between optical system 10 and interior chamber 60 of reactor 30, a radiation-transparent region, in the current example an IR-transparent region 20, is provided that, in the current example represents a part of the wall of reactor 30 in the embodiment of an IR-transparent glass tube. IR-light source 10 is protected by IR-transparent region 20 from the medium that is to be heated and which flows through interior chamber 60 of reactor 30. In the illustrated example, IR-transparent region 20 extends along the entire length L of reactor 30. Because of this, the IR-radiation emitted from IR-light source 10 can enter interior chamber 60 of reactor 30 at the highest level possible. Optical system 10 in the illustrated embodiment is an IR-lamp, in other words an undirected light source. For this case it is especially preferred to provide a lamp reflector 70. According to the invention more than one IR-light source may of course be utilized. Other types of lamp are also possible. If, for example IR-LEDs are used, these would be directed light sources, so that a lamp reflector in this case could be omitted without jeopardizing the desired high homogeneity of the radiation distribution. In the illustrated example, the first reflector in the form of IR-reflecting coating 67 is in direct contact with second reflector 70, so that an aggregate reactor is created from both. In the current embodiment the reactor is also divided into 2 functional regions F1 and F2. In this particular embodiment, functional region F2 begins where reflector 67 begins.

The systems according to the current invention therefore, unexpectedly show a radiation distribution which, at no point in the medium-conducting interior chamber in the reactor exhibit depletion zones. Relatively high radiation values can be achieved over the entire reactor cross section. Moreover, an especially high compactness of the system is provided.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

COMPONENT IDENTIFICATION LIST

1 UV-light source from current state of the art
5 encasement tube from current state of the art
7 tube or UV-reactor from current state of the art
10 optical system
20 radiation-transparent region or radiation-transparent window
30, 30.1, 30.2, 30.3, 30.4 reactor
32, 32a, 32b, 32.1, 32.2, 32.3, 32.4 lateral surfaces
34, 34a, 34b, 34.1, 34.2, 34.3, 34.4 lateral surfaces
35 arrow for direction of flow
40, 40.1, 40.2, 40.3, 40.4 part, connecting the lateral surfaces or connecting part
50 part, connecting the lateral surfaces or inlet part
55 structural transition, corner
55.1, 55.2 corner
60, 60.1, 60.2, 60.3, 60.4 interior chamber
65 radiation-reflecting inside layer or radiation-reflecting inside coating
67 radiation-reflecting outside layer or radiation-reflecting outside coating
70 reflector (second or lamp reflector)
A1, A2, A3, . . . distance in functional region F2
B1, B2, . . . distance in functional region F1
F1 first functional region
F2, F2.1, F2.2, F2.3, F2.4 second functional region

What is claimed is:
1. A system for treating gasses and/or liquids with radiation or for detecting radiation in gasses and/or liquids, comprising:
at least one optical system;
a reactor, said reactor being in the form of a cylindrical hollow body having a first pair of lateral surfaces and a second pair of lateral surfaces connected to said first pair of lateral surfaces;
a connecting part connecting said second pair of lateral surfaces;
an inlet part connecting said first pair lateral surfaces, said inlet part is in the form of a radiation-transparent region in the form of a radiation-transparent window provided at said inlet part of said reactor, said radiation-transparent window extending across a full length of the reactor;

an interior chamber which is open at a front end and at a rear end and through which a medium flows or in which a medium is present;
said reactor being designed at least partially as a first reflector which reflects radiation emitted by or for said at least one optical system;
said reactor being divided into a first functional region associated with said first pair of lateral surfaces and at least one second functional region associated with said second pair of lateral surfaces and connected to said first functional region, said first functional region being located nearer to said at least one optical system than said at least one second functional region;
said first functional region and said at least one second functional region being configured so that
the distance between said first pair of lateral surfaces located opposite one another within said first functional region increases so that radiation therein can spread substantially unimpeded and
the distance between said second pair lateral surfaces located opposite one another within said at least one second functional region decreases continuously with increasing distance to said at least one optical system so that overlays of said radiation occur.

2. The system according to claim 1, wherein:
said optical system being selected from one of a UV light source, an IR light source, an optical measuring device, and an optical sensor.

3. The system according to claim 1, wherein:
said at least one optical system being arranged outside said reactor; and
a radiation-transparent window forming said inlet part of said reactor and separating said optical system from said interior chamber.

4. The system according to claim 1, wherein:
said second pair of lateral surfaces and said connecting part being designed as said first reflector.

5. The system according to claim 1, wherein:
said first reflector being one of a radiation-reflecting material, a radiation-reflecting material combination, a radiation-reflecting inside layer, a radiation-reflecting inside coating, a radiation-reflecting outside layer, and a radiation-reflecting outside coating.

6. The system according to claim 1, wherein:
said at least one optical system being arranged outside said reactor; and
a second reflector being assigned to said at least one optical system.

7. The system according to claim 6, wherein:
said second pair of lateral surfaces and said connecting part forming said first reflector; and
said first reflector and said second reflector forming an aggregate reflector.

8. The system according to claim 1, wherein:
a homogeneity of said radiation emitted from or for said at least one optical system being expressed by a standard deviation from the mean value of a radiation density in said reactor being less than 30%.

9. The system according to claim 8, wherein:
said homogeneity of said radiation emitted from or for said at least one optical system being expressed by said standard deviation from the mean value of said radiation density in said reactor being less than 25%.

10. The system according to claim 9, wherein:
said homogeneity of said radiation emitted from or for said at least one optical system being expressed by said standard deviation from the mean value of said radiation density in said reactor being less than 20%.

11. The system according to claim 10, wherein:
said homogeneity of said radiation emitted from or for said at least one optical system being expressed by said standard deviation from the mean value of said radiation density in said reactor being less than 15%.

12. The system according to claim 11, wherein:
said homogeneity of said radiation emitted from or for said at least one optical system being expressed by said standard deviation from the mean value of said radiation density in said reactor being less than or equal to 13%.

13. The system according to claim 12, wherein:
said homogeneity of said radiation emitted from or for said at least one optical system being expressed by said standard deviation from the mean value of said radiation density in said reactor being less than or equal to 10%.

14. The system according to claim 1, wherein:
a proportion of volume of said interior chamber to overall volume of said system being at least approximately 60%.

15. The system according to claim 14, wherein:
a proportion of volume of said interior chamber to overall volume of said system being at least approximately 70%.

16. The system according to claim 15, wherein:
a proportion of volume of said interior chamber to overall volume of said system being at least approximately 80%.

17. The system according to claim 16, wherein:
a proportion of volume of said interior chamber to overall volume of said system being at least approximately 90%.

18. A system for treating gasses and/or liquids with radiation or for detecting radiation in gasses and/or liquids, comprising:
at least one optical system;
a plurality of reactors, each said reactor being in the form of a cylindrical hollow body having lateral surfaces, each said reactor being designed at least partially as a first reflector which reflects radiation emitted by or for said at least one optical system, and said plurality of reactors defining a first functional region and a plurality of second functional regions, said first functional region is located nearer to said at least one optical system than each said second functional region of said plurality of second functional regions, each said reactor including:
an interior chamber which is open at a front end and at a rear end and through which a medium flows or in which a medium is present; and
a radiation-transparent region concentric with and surrounding said at least one optical system, said radiation-transparent region extending across a full length of the reactor, wherein a distance between each said lateral surfaces located opposite one another within each said second functional region of said plurality of second functional regions decreases so that overlays of said radiation occur.

19. The system according to claim 18, wherein said plurality of reactors are combined together such that each of said interior chambers of said plurality of reactors are combined in the form of a common interior chamber.

20. The system according to claim 18, wherein said radiation-transparent region is located at a distance from said at least one optical system such that said radiation-transparent region encompasses said first functional region and that each of said interior chambers of said plurality of reactors are in the form of separate interior chambers, and said medium flows through said separate interior chambers.

* * * * *